United States Patent
Pei

(10) Patent No.: US 11,006,296 B2
(45) Date of Patent: May 11, 2021

(54) IMPLANTABLE MEDICAL DEVICE AND METHOD FOR MEASURING COMMUNICATION QUALITY

(71) Applicant: PACESETTER, INC., Sylmar, CA (US)

(72) Inventor: Xing Pei, Thousand Oaks, CA (US)

(73) Assignee: PACESETTER, INC., Sylmar, CA (US)

( * ) Notice: Subject to any disclaimer, the term of this patent is extended or adjusted under 35 U.S.C. 154(b) by 221 days.

(21) Appl. No.: 16/195,704

(22) Filed: Nov. 19, 2018

(65) Prior Publication Data

US 2020/0162948 A1 May 21, 2020

(51) Int. Cl.
*H04W 24/08* (2009.01)
*H04B 17/318* (2015.01)
*H04B 17/364* (2015.01)
*A61B 5/00* (2006.01)
*A61N 1/372* (2006.01)
*A61N 1/39* (2006.01)
*H04L 12/26* (2006.01)

(52) U.S. Cl.
CPC .......... *H04W 24/08* (2013.01); *A61B 5/0006* (2013.01); *A61N 1/37223* (2013.01); *A61N 1/3937* (2013.01); *H04B 17/318* (2015.01); *H04B 17/364* (2015.01); *H04L 43/045* (2013.01); *A61N 1/3956* (2013.01)

(58) Field of Classification Search
None
See application file for complete search history.

(56) References Cited

U.S. PATENT DOCUMENTS 5,176,138 A * 1/1993 Thacker ............. A61N 1/36557
607/18
7,785,256 B1 * 8/2010 Koh ..................... A61B 5/7445
600/300

(Continued)

FOREIGN PATENT DOCUMENTS

KR 20120119625 A 10/2012

OTHER PUBLICATIONS

International Search Report and Written Opinion for Corresponding Application No. PCT/US2019/060650 dated Apr. 17, 2020 (16 pages).

*Primary Examiner* — Kodzovi Acolatse
(74) *Attorney, Agent, or Firm* — The Small Patent Law Group LLC; Dean D. Small

(57) ABSTRACT

A method for determining quality of a communications link between an external instrument (EI) and an implantable medical device (IMD) is provided. The method includes receiving, with a receiver of an EI, data packets sent at intervals from an IMD and determining, with a processor of the EI, an expected time interval between a first data packet and a second data packet. The processor of the EI determines a difference between the expected time interval between the first data packet and the second data packet and an actual time interval between the first data packet and the second data packet. The processor of the EI also provides a time variant communication quality indicator based on the difference between the expected time interval between the first data packet and the second data packet and the actual time interval between the first data packet and the second data packet.

24 Claims, 6 Drawing Sheets

(56) References Cited

U.S. PATENT DOCUMENTS

| | | | |
|---|---|---|---|
| 9,782,595 B2* | 10/2017 | Greene | A61N 1/37252 |
| 9,889,305 B1* | 2/2018 | Hellman | A61B 5/0402 |
| 2003/0112758 A1* | 6/2003 | Pang | H04J 3/14 |
| | | | 370/235 |
| 2005/0222789 A1* | 10/2005 | West | G11C 29/56 |
| | | | 702/79 |
| 2007/0253337 A1 | 11/2007 | Morinaga et al. | |
| 2008/0033494 A1* | 2/2008 | Swerdlow | A61B 5/046 |
| | | | 607/5 |
| 2010/0121413 A1 | 5/2010 | Willerton et al. | |
| 2013/0261686 A1* | 10/2013 | Swerdlow | A61N 1/3987 |
| | | | 607/8 |
| 2014/0328205 A1 | 11/2014 | Scherecke et al. | |
| 2015/0148868 A1* | 5/2015 | Shahandeh | A61N 1/37217 |
| | | | 607/60 |
| 2016/0310733 A1* | 10/2016 | Sheldon | A61N 1/368 |
| 2017/0113050 A1* | 4/2017 | Brisben | A61N 1/3704 |
| 2017/0216611 A1* | 8/2017 | Yoder | A61N 1/37254 |
| 2018/0020931 A1* | 1/2018 | Shusterman | A61B 5/02125 |
| | | | 600/483 |
| 2018/0028827 A1* | 2/2018 | Schilling | A61N 1/37264 |
| 2018/0243577 A1* | 8/2018 | Kivi | A61N 1/37276 |
| 2019/0164563 A1* | 5/2019 | Volcker | H04L 12/1827 |
| 2019/0175040 A1* | 6/2019 | Arcot Desai | A61B 5/0478 |

* cited by examiner

IMPLANTABLE MEDICAL DEVICE AND METHOD FOR MEASURING COMMUNICATION QUALITY

BACKGROUND

Embodiments of the present disclosure generally relate to systems and methods for establishing a communication link between devices, and more particularly to measuring the communication quality within communication links between implantable medical devices and external instruments.

An implantable medical device (IMD) is a medical device that is configured to be implanted within a patient anatomy and commonly employs one or more leads with electrodes that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external instrument as well as control patient therapy. The components of the IMD are hermetically sealed within a metal housing.

IMDs are programmed by, and exchange data with, external instruments controlled by physicians and/or the patient. The external instruments use proprietary or commercial operating systems (e.g., iOS, Android) that communicate through wireless bi-directional communication links with the IMDs. The quality of the communication pathway of the bi-direction communication link is affected by noise, either internal or environmental, that causes interference with a transmitted communication signal, as well as signal strength and receiving sensitivity. The noise can cause significant issues and concerns when increased amounts of data need to be transferred during certain procedures.

The communication quality is particularly important for implantable cardiac systems. During a critical task, such as induction during an implant scenario to determine the defibrillation threshold, a real-time test to evaluate heart function, communication between the external instrument and implanted device determines if the test will be successful and a risk to the patient. Before starting such evaluation/test, the clinician typically examines the communication quality and ensures it indicates a good communication condition.

However, current methods used to determine communication quality are based on the quality of the signal received by the implanted device prior to the implanted device transmitting a signal to the external instrument. Typically, the quality of the signal received by a transmitting device is a good indicator of the quality of the signal that will transmitted, but when in a medical setting, such as when taking a real-time test to evaluate heart function, greater accuracy is desired.

BRIEF SUMMARY

In accordance with embodiments herein, a method for determining quality of a communications link between an external instrument (EI) and an implantable medical device (IMD) is provided. The method includes receiving, with a receiver of an EI, data packets sent at intervals from an IMD. The method also includes determining, with a processor of the EI, an expected time interval between a first data packet and a second data packet, and determining, with the processor of the EI, a difference between the expected time interval between the first data packet and the second data packet and an actual time interval between the first data packet and the second data packet. The processor of the EI also provides a time variant communication quality indicator based on the difference between the expected time interval between the first data packet and the second data packet and the actual time interval between the first data packet and the second data packet.

In accordance with embodiments herein, a method for determining quality of a communications link between an external instrument (EI) and an implantable medical device (IMD) is provided. The method includes receiving, with a receiver of an EI, data packets sent at intervals from an IMD, determining, with a processor of the EI, the difference in time between a subsequent data packet and a previous data packet, and providing, with the processor of the EI, a time variant communication quality indicator based the difference in time between the subsequent data packet and the previous subsequent data packet. The method also includes determining, with the processor of the EI, a relative received signal strength indicator (RSSI) of the subsequent data packet received by the receiver of the EI and the received signal strength indicator (RSSI) from the implantable medical device (IMD), and calculating, with the processor of the EI, a RSSI communication quality indicator based on the RSSI of the subsequent data packet received by the receiver of the EI. The method also includes comparing, with the processor of the EI, the time variant communication quality indicator and the RSSI communication quality indicator, and selecting, with the processor of the EI, one of the time variant communication quality indicator and the RSSI communication quality indicators, or the weighed combination of the three, to present to a user.

In accordance with embodiments herein, an external instrument (EI) that monitors an implantable medical device (IMD) is provided. The EI includes a receiver for receiving data packets periodically sent by the IMD. The EI also includes a processor configured to determine a communication quality indicator based on delays between data packets received by the EI.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Various embodiments described herein include a method and/or system to determine the quality of communication of a wireless bi-directional communication link between an implantable medical device (IMD) and an external instrument (EI). The EI determines the time between each signal received from the IMD compared to when the signal should have been received. Then, based on the variance of the timing of the received signals a communication quality indicator is formed. Optionally, at the same time, relative received signal strength (RSSI) is utilized to also form a communication quality indicator. The communication quality indicators are then compared and the minimal indicator is presented to a user to allow them to make decisions related to the quality of the communication link and the amount of data that may be transferred while taking measurements from the IMD.

Figure 1:
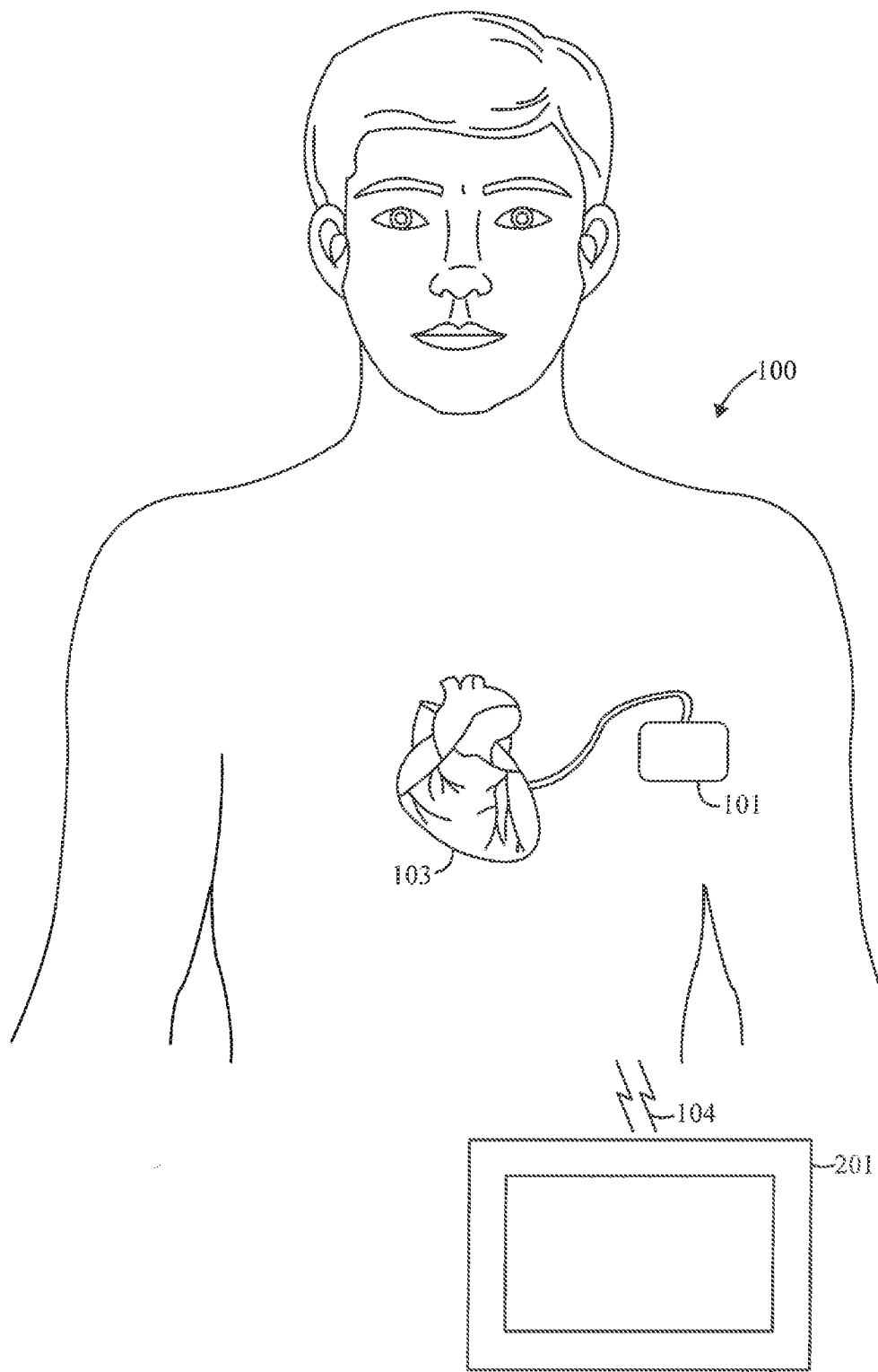
FIG. 1 illustrates simplified block diagram of a system for initiating a bi-directional communication link, according to an embodiment herein.

FIG. 1 illustrates a simplified block diagram of a system 100 for initiating a bi-directional communication link. The system 100 includes an IMD 101 and an EI 201 (e.g., table computer, smart phone, smart watch, laptop, and/or the like), according to an embodiment. The IMD 101 may be implanted within a patient (e.g., proximate to and/or within a heart 103, proximate to the spinal cord). Additionally, or alternatively, the IMD 101 may have components that are external to the patient, for example, the IMD 101 may include an external pulse generator (EPG). Optionally, the IMD 101 may be one of various types of implantable devices, such as, for example, neurostimulator, patient, an implantable pacemaker, implantable cardioverter-defibrillator (ICD), defibrillator, cardiac rhythm management (CRM) device, an implantable pulse generator (IPG), or the like.

Optionally, the IMD 101 may be a leadless pacer, examples of which are disclosed in U.S. Pat. No. 9,072,913, entitled, "RATE RESPONSIVE LEADLESS CARDIAC PACEMAKER," and U.S. Pat. No. 9,168,383, entitled "LEADLESS CARDIAC PACEMAKER WITH CONDUCTED COMMUNICATION," METHOD OF FABRICATING STIMULATION LEAD FOR APPLYING ELECTRICAL STIMULATION TO TISSUE OF A PATIENT," which are expressly incorporated herein by reference. Additionally, or alternatively, the IMD 101 may be a leadless monitor, examples of which are disclosed in U.S. Pat. No. 9,949,660, entitled, "METHOD AND SYSTEM TO DISCRIMINATE RHYTHM PATTERNS IN CARDIAC ACTIVITY," which is expressly incorporated herein by reference.

The EI 201 is configured to establish a wireless bi-directional communication link 104 with the IMD 101. The communication link 104 allows the EI 201 to receive measurements from the IMD 101, and to program or send instructions to the IMD 101. The communication link 104 may use a standard wireless protocol such as Bluetooth Low Energy, Bluetooth, Medical Implant Communication Service, and/or the like. The EI 201 may be located within a home of the patient, a hospital, an automobile, at an office of the patient, or the like.

Figure 2:
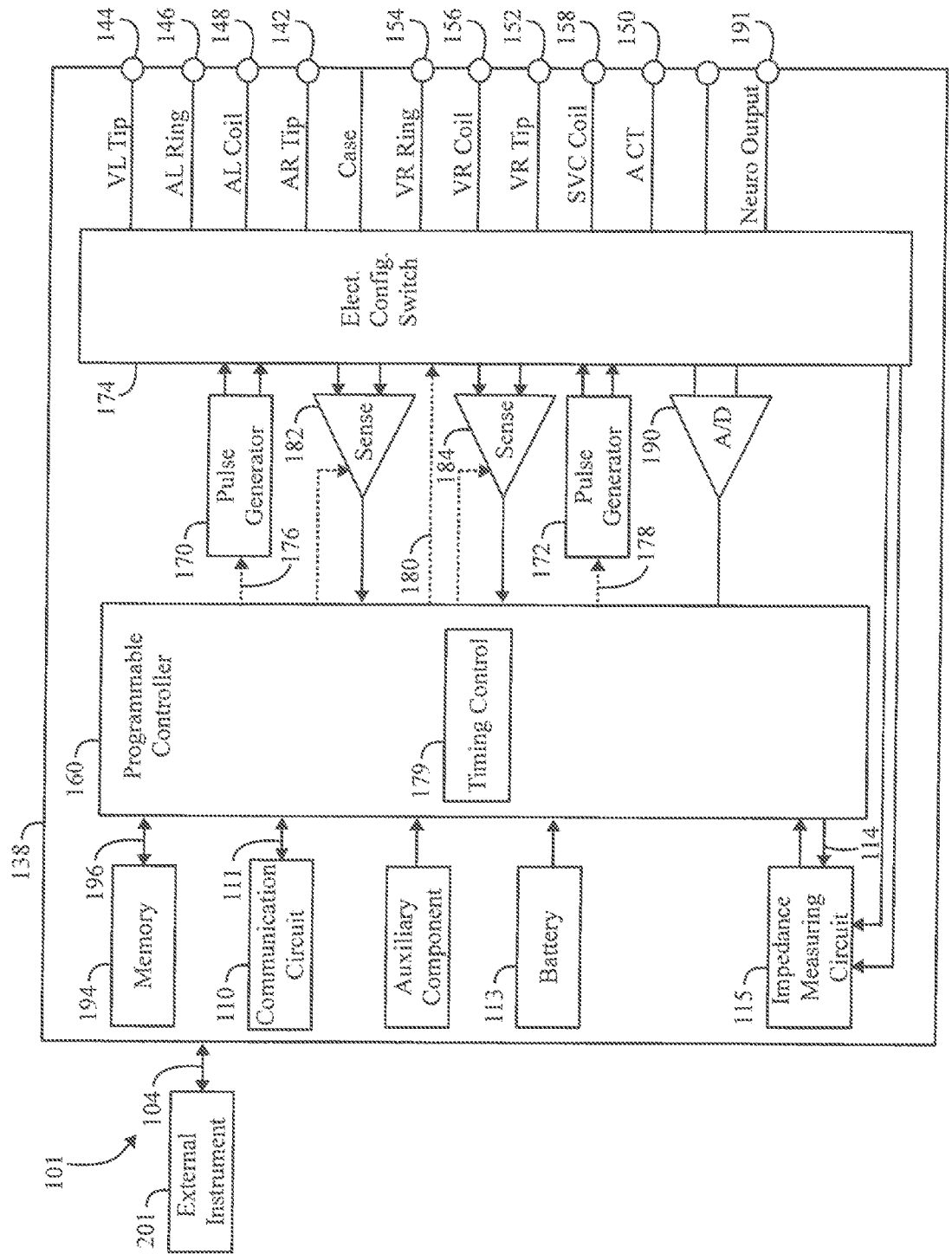
FIG. 2 illustrates a block diagram of an implantable medical device formed in accordance with embodiments herein.

FIG. 2 illustrates a block diagram of internal components of the IMD 101. The components described herein can include or represent hardware and software instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

The IMD 101 is for illustration purposes only, and it is understood that the circuitry could be duplicated, eliminated or disabled in any desired combination to provide a device capable of treating the appropriate heart chamber(s) with cardioversion, defibrillation and/or pacing stimulation as well as providing for apnea detection and therapy. Additionally, or alternatively, the IMD 101 may be used to generate neurostimulation for application to a desired area of a body, such as a spinal cord stimulation, the brain and the like.

The housing 138 for the IMD 101, shown schematically in FIG. 2, is often referred to as the "can", "case" or "case electrode" and may be programmably selected to act as the return electrode for all "unipolar" modes. The housing 138 may further be used as a return electrode alone or in combination with one or more of the coil electrodes for shocking purposes. The housing 138 further includes a connector (not shown) having a plurality of terminals. The terminals may be configured to be coupled to different types of electrodes and leads. FIG. 2 illustrates various non-limiting examples of types/positions of electrodes that may be utilized. All or a portion of the terminals may be used in various combinations. It is recognized that alternative types of electrodes may be utilized in place of, or in addition to, the examples of FIG. 2. The following examples are provided as non-limiting examples of terminals: 142 (right atrial tip electrode), 144 (left ventricular tip electrode), 146 (left atrial ring electrode), 148 (left atrial coil electrode), 150 (acoustical terminal, ACT electrode), 152 (ventricular tip electrode), 154 (right ventricular ring electrode), 156 (right ventricular coil electrode), and 158 (superior vena cava coil electrode). In addition, a terminal 191 is indicated to be representative of one or more neural stimulation electrodes that may be utilized in place of or in addition to the above noted electrodes.

The IMD 101 includes a controller circuit 160 which controls operation of the IMD 101. The controller circuit 160 (also referred to herein as a processor module or unit) may include one or more processors, or equivalent control circuitry, designed specifically for controlling the delivery of stimulation therapy and may further include RAM or ROM memory, logic and timing circuitry, state machine circuitry, and I/O circuitry. Typically, the controller circuit 160 includes the ability to process or monitor input signals (data) as controlled by program code stored in memory. The details of the design and operation of the controller circuit 160 are not critical to the invention. Rather, any suitable controller circuit 160 may be used that carries out the functions described herein. Among other things, the controller circuit 160 receives, processes, and manages storage of digitized cardiac data sets from the various sensors and electrodes. For example, the cardiac data sets may include IEGM data, pressure data, heart sound data, and the like.

The IMD 101 includes pulse generators 170, 172 to generate stimulation pulses for delivery by one or more leads and/or electrodes. The stimulation may be configured in different manners, such as in connection with neural stimulation, pacing pulse stimulation, cardioversion stimulation, defibrillation shocks, and the like. The pulse generators, 170 and 172, may include dedicated, independent pulse generators, multiplexed pulse generators or shared pulse generators. The pulse generators, 170 and 172, are controlled by the controller circuit 160 via appropriate control signals, 176 and 178, respectively, to trigger or inhibit the stimulation pulses.

The pulse generators 170, 172 may be represent atrial and/or ventricular pulse generators, where the stimulation pulses are delivered through a plurality of electrodes and/or leads located within or proximate to the heart. Optionally, the pulse generators 170, 172 may represent neurostimulation pulse generators to generate stimulation pulses for a brain or spinal cord nervous system. The stimulation pulses are delivered by a plurality of electrodes through the neuro output lead 191. The neuro stimulation pulse generator circuit is controlled by the controller circuit 160 via appropriate control signals to trigger or generate the stimulation pulses.

The controller circuit 160 further includes timing control circuitry 179 used to control the timing of such stimulation pulses (e.g., the neural stimulation waveforms, pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 174 includes a plurality of switches for connecting the desired electrodes to the appropriate I/O circuits, thereby providing complete electrode programmability. Accordingly, the switch 174, in response to a control signal 180 from the controller circuit 160, determines the polarity of the stimulation pulses (e.g., unipolar, bipolar, etc.) by selectively closing the appropriate combination of switches (not shown).

A sensing circuit 182 and sensing circuit 184 may also be selectively coupled to one or more leads through the switch 174 for collecting sensed physiologic data (e.g. cardiac activity, neural activity, respiratory activity, etc.). The sensing circuits, 182 and 184, may include dedicated sense amplifiers, multiplexed amplifiers or shared amplifiers. The outputs of the sensing circuits, 182 and 184, are connected to the controller circuit 160 which, in turn, receives the sensed data and is able to trigger or inhibit the pulse generators, 170 and 172, respectively, in a demand fashion in response to the absence or presence of activity of interest.

Sensed signals are also applied to the inputs of an analog-to-digital (ND) data acquisition system 190. The data acquisition system 190 is configured to acquire IEGM signals, neural signals, and the like. The data acquisition system 190 converts the raw analog data into a digital signal, and store the digital signals in memory 194 for later processing and/or communication transmissions such as Radio Frequency (RF) transmission to the EI 201. The data acquisition system 190 is coupled to one or more leads through the switch 174 to sample signals across any combination of desired electrodes. The data acquisition system 190 may also be coupled, through switch 174, to one or more of the acoustic sensors. The data acquisition system 190 acquires, performs ND conversion, produces and saves the digital pressure data, and/or acoustic data.

A communication circuit 110, such as an RF circuit, may be configured to handle and/or manage the bi-directional communication link between the IMD 101 and the EI 201. As explained herein, the communication circuit 110 transmits, data to the EI 201. The communication circuit 110 also scans for connection requests from the EI 201. The communication circuit 110 is controlled by the controller circuit 160 and may support one or more wireless communication protocols while communicating with the EI 201, such as Bluetooth low energy, Bluetooth, Medical Implant Communication Service (MICS), and/or the like. The communication circuit 110 may include a transmitter, receiver, and/or a transceiver. Optionally, the communication circuit 110 may be electrically coupled to an antenna (not shown). Protocol firmware may be stored in memory 194, which is accessed by the controller circuit 160. The protocol firmware provides the wireless protocol syntax for the controller circuit 160 to assemble data packets, connection requests, connection responses, establish communication links 104, and/or partition data received from the EI 201.

The controller circuit 160 is coupled to the memory 194 by a suitable data/address bus 196, wherein the programmable operating parameters used by the controller circuit 160 are stored and modified, as required, in order to customize the operation of IMD 101 to suit the needs of a particular patient. The memory 194 also stores data sets (raw data, summary data, histograms, etc.), such as the IEGM data, heart sound data, pressure data, CO2 data, temperature data and the like for a desired period of time (e.g., 1 hour, 24 hours, 1 month). The pacing and other operating parameters of the IMD 101 may be non-invasively programmed into the memory 194 through the communication circuit 110 in bi-directional wireless communication with the EI 201. The communication circuit 110 is controlled by the controller circuit 160 and receives data for transmission over a control line 111. The communication circuit 110 allows intra-cardiac electrograms, pressure data, acoustic data, CO2 data, and status information relating to the operation of IMD 101 (as contained in the controller circuit 160 or memory 194) to be sent to the EI 201 through an established bi-directional communication link 104.

The IMD 101 additionally includes a battery 113, which provides operating power to all of the circuits shown. Optionally, the IMD 101 may include an impedance measuring circuit 115 which is enabled by the controller circuit 160 via a control signal 114. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be will soon as the obtained.

Figure 3:
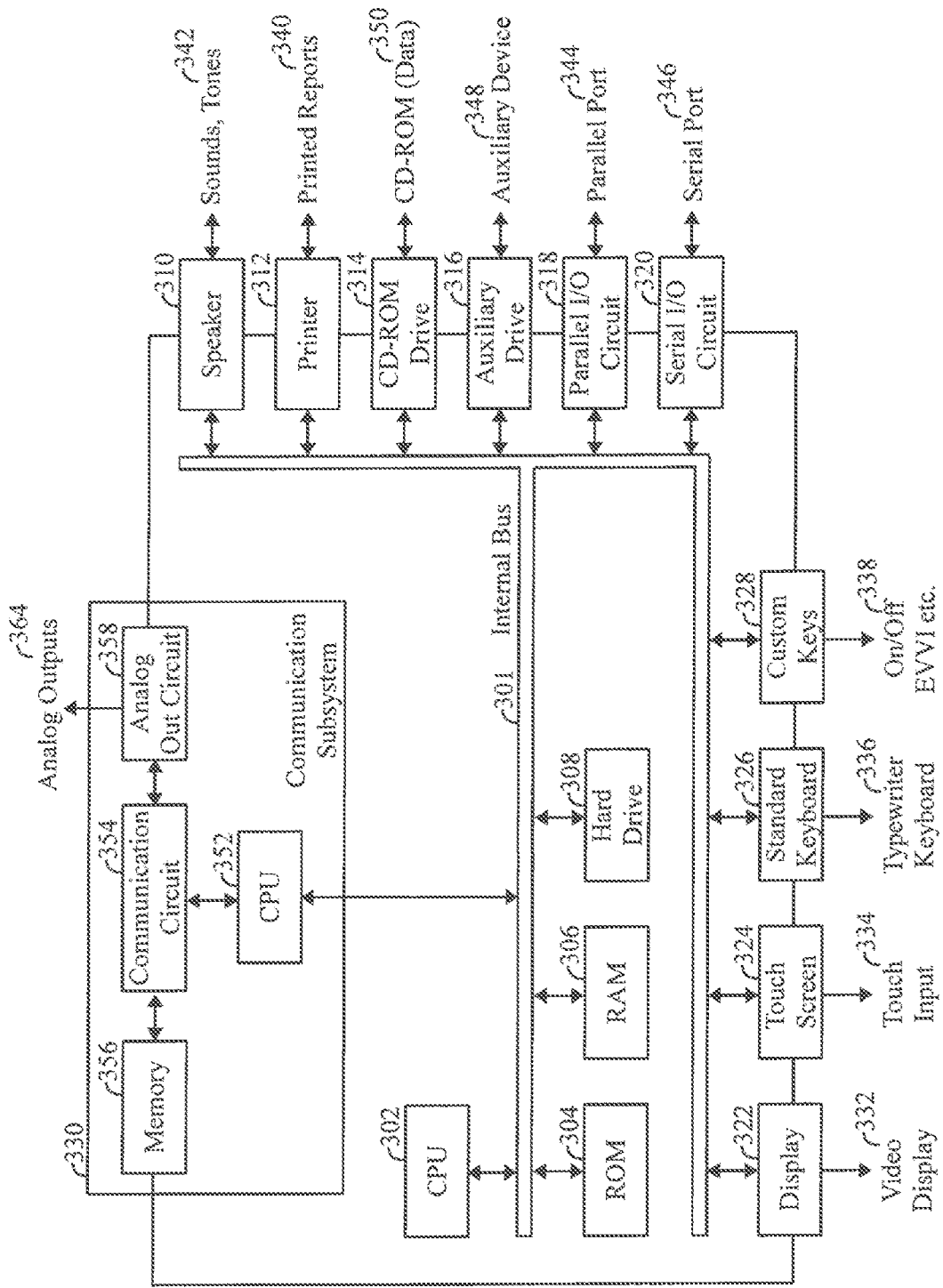
FIG. 3 illustrates a block diagram of an external instrument operated in accordance with embodiments herein.

FIG. 3 illustrates a functional block diagram of the EI 201 that is operated in accordance with embodiments herein. The EI 201 may be a workstation, a portable computer, a tablet computer, a smart watch, an IMD programmer, a PDA, a cell phone and/or the like. The EI 201 may include an internal bus 301 that may connect/interface with a Central Processing Unit ("CPU") 302, ROM 304, RAM 306, a hard drive 308, a speaker 310, a printer 312, a CD-ROM drive 314, an auxiliary drive 316, a parallel I/O circuit 318, a serial I/O circuit 320, the display 322, a touchscreen 324, a standard keyboard 326, custom keys 328, and an communication subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a micro-controller, or equivalent control circuitry, designed specifically to control interfacing with the EI 201 and with the IMD 101. The CPU 302 may include RAM or ROM memory, logic and timing circuitry, state machine circuitry, and I/O circuitry to interface with the IMD 101. The display 322 (e.g., may be connected to the video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the EI 201 when selections are made by the user. Optionally the touchscreen 324 may be integrated with the display 322. The keyboard 326 (e.g., a typewriter keyboard 336) allows the user to enter data to the displayed fields, as well as interface with the communication subsystem 330. Furthermore, custom keys 328 turn on/off 338 (e.g., EVVI) the EI 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. The auxiliary drive 316 such as a floppy drive accepts auxiliary devices 348 such as diskettes. Optionally, the serial I/O port may be coupled to a USB port or other interface capable of communicating with a USB device such as a memory stick. The CD-ROM drive 314 accepts CD ROMs 350. One or more scanning schedules are stored in the RAM 306, ROM 304, on a CD ROM 350, or elsewhere.

The communication subsystem 330 includes a central processing unit (CPU) 352 in electrical communication with a communication circuit 354, which may communicate with both memory 356 and an analog out circuit 358. The analog out circuit 358 includes communication circuits to communicate with analog outputs 364. The EI 201 may wirelessly communicate with the IMD 101 and utilize protocols, such as Bluetooth, Bluetooth low energy, MICS, and/or the like. For example, the memory 356, ROM 304, and/or RAM 306 may include Protocol firmware, which is accessed by the CPU 352 and/or 302. The protocol firmware provides the wireless protocol syntax for the CPU 352 and/or 302 160 to assemble data packets, establish communication links 104, and/or partition data received from the IMD 101. The communication subsystem 330 and CPU 352 enter scanning states and establish communication sessions as described herein.

Signal Timing and Signal Quality Management

Figure 4:
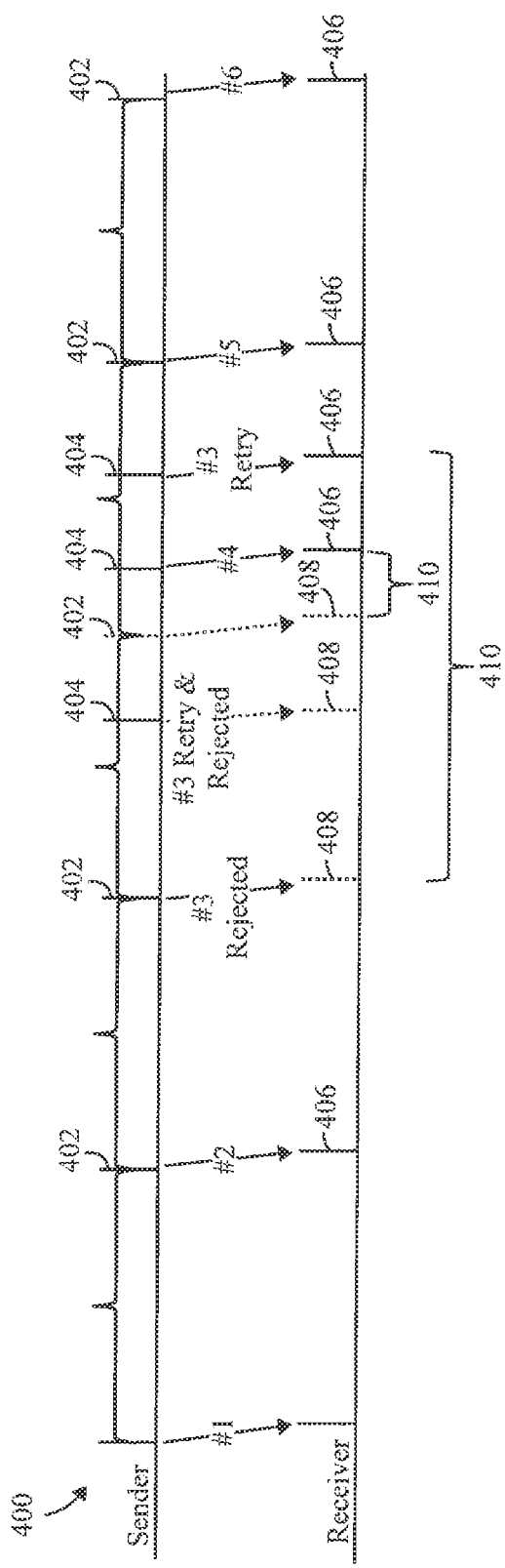
FIG. 4 is a timing diagram for establishing the wireless bi-directional communication link between the IMD and the EI in accordance with embodiments herein.

FIG. 4 is a timing diagram 400 illustrating transmitted data packets 402, retransmitted data packets 404 transmitted by the IMD 101, received data packets 406, and delayed and/or missed data packets 408 received by the EI 201. Specifically, the communication subsystem 330, including the CPU 352 and communication circuit 354 receive the transmitted data packets 402, retransmitted data packets 404, and determine when a missed packet 408 occurs. In one example of the transmission of the data packets 402 and retransmitted data packets 404, the communication subsystem 330 of the EI 201 and the IMD 101 may utilize the Bluetooth Low Energy ("BLE") protocol. The BLE protocol is defined within "Bluetooth Specification Version 4.1," published Dec. 3, 2013 (incorporated herein by reference). In another example, there may be a number of retries that may further delay the transmission and may also impact next to be transmitted signal to be late. In yet another example, there may be a number of retries that may further delay the transmission and may result a different order of data transmission that need to be corrected in the receiving side.

When delayed and/or missed data packets 408 occur as a result of noise, interference, or the like that blocks the transmitted data packet, the EI 201 communicates with the IMD that a data packet has not be received at an expected time and the IMD 101 in response provides a retransmitted data packet 404 to be received by the EI 201. FIG. 4 illustrates the blocked transmitted data packet 402 as a missed data packet 408. When a missed data packet 408 occurs, a delay 410 in receipt of the received data packet 406 similarly occurs and is represented as the amount of time that lapses from the missed data packet 408 to the receipt of the received data packet 406. Specifically, because in the medical setting the IMD 101, and the EI 201 are a relatively fixed distance from one another and generally do not move, and because testing requires the transmitted data packets 402 be sent at constant time intervals, pre-determined time intervals, or pre-negotiated time intervals to eliminate as many variables in a test as possible, the only variable affecting the timing of the received data packets 406 are the missed data packets 408. Consequently, the time variation of the time intervals is inversely proportion to the quality of the communication. Specifically, because missed data packets 408 are due to interference and noise, variance detected in the time intervals is indicative of the quality of the communication.

In certain special conditions, when there is a large amount of data that needs to be transmitted at the same time, the IMD may need to purposely delay the periodic transmission/pre-determined transmission. In certain special conditions, when there is a more time, critical execution is needed for the IMD, and the IMD may need to purposely delay the periodic transmission/pre-determined transmission. When these types of conditions occur, the IMD can communicate with the external instrument to re-define the timing so that the variance in transition is known to change to external instrument. In addition, when there is a large amount data transmitted, the external instrument can omit the variance that is the indication of quality, because the successful transmission of the large data block is an indication of good communication quality. In particular, if the periodic transmission of a large data block occurs, then an indication is provided that communication quality is good.

Figure 5:
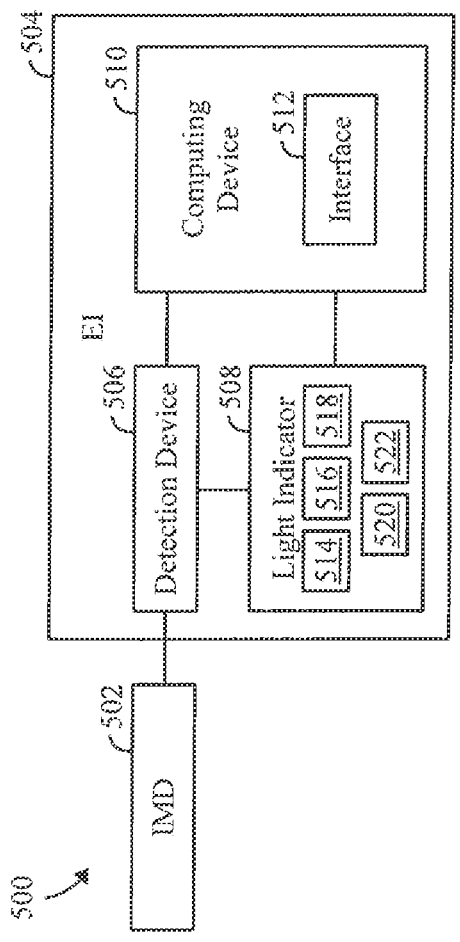
FIG. 5 illustrates a block diagram of a signal quality management system in accordance with embodiments herein.

FIG. 5 illustrates an example schematic diagram of a signal quality management system 500. The signal quality management system 500 includes an IMD 502 and an EI 504. The EI includes a detection device 506, a light indicator 508, and a computing device 510 with an interface 512.

As a result of the general inverse relationship of the variance in time intervals and quality of the communication link, time intervals are measured, and pre-determined results are provided as rankings associated with light produced by the light indicator 508 and/or a number displayed on the interface 512 of the computing device. The rankings are then utilized as a tool to determine if the IMD 502 can successfully manage the volume of data required for a procedure in a noisy environment. Specifically, in the example embodiment, a five bar communication quality indicator is provided with six (6) states that are associated with five (5) independently operated lights 514, 516, 518, 520, 522 of the light indicator 508. Thus, no lights showing represents the worst quality of the communication link, five (5) lights represent the best quality of communication link, with each successive light illuminating from zero (0) to five (5) indicating a higher degree of quality. Similarly, on the interface 512 a numeral zero to five (0-5), a color code bar, or the like can be provided to indicate the quality of the communication link.

In one example the IMD 502 is an ICD that streams intracardiac electrograms (IEGM), one (1) data packet every 48 milliseconds. Each data packet includes a unique identifier such as a sequence number of the packet so that the EI 504 can re-arrange the data based on the unique identifier, even if the packet may not arrive in order due to a retransmission. The table below illustrates such a data in table form.

column is the real-time interval from zero a data packet is received. Thus, transmitted data packet 1 is received 48 ms after the start, transmitted data packet 2 is received 103 ms after the start, transmitted data packet 3 is received 144 ms after the start, and the like. Column 5, the "delta arriving time" represents the difference in time (in ms) between received data packets. Consequently, the difference in time between the start and the first received data packet is 48 ms; the difference in time between the second received data packet (103 ms) and the first received data packet (48 ms) is 55 ms; the difference in time between the third received data packet (144 ms) and the second received data packet (103 ms) is 41 ms; and the like.

Columns 6, 7 and 8 of Table 1 represent information generated by an algorithm of a processer that reorders the received data packets based on their unique identifier. Column 6, the "packet received reorder" column is the placement of the data packets received in the order the data packets were transmitted according to the unique identifier

TABLE 1

| Packet To Be Sent | Sent Timing (ms) | Packet Received | Received Timing (ms) | Delta Arrival Timing | Packet Received Reordered | Received Timing Reordered | Delta from Expected Timing | Comment |
|---|---|---|---|---|---|---|---|---|
| 0 | 0 | 0 | 0 | 0 | 0 | 0 | 0 | No Retry |
| 1 | 48 | 1 | 48 | 48 | 1 | 48 | 0 | No Retry |
| 2 | 98 | 2 | 103 | 55 | 2 | 103 | 7 | Retry |
| 3 | 144 | 3 | 144 | 41 | 3 | 144 | 0 | No Retry |
| 4 | 192 | 4 | 192 | 48 | 4 | 192 | 0 | No Retry |
| 5 | 240 | 5 | 320 | 128 | 5 | 330 | 90 | Retry |
| 6 | 288 | 6 | 330 | 10 | 6 | 320 | 32 | Retry |
| 7 | 336 | 7 | 336 | 6 | 7 | 336 | 0 | No Retry |
| 8 | 384 | 8 | 384 | 48 | 8 | 384 | 0 | No Retry |
| 9 | 432 | 9 | 474 | 90 | 9 | 474 | 42 | Retry |
| 10 | 480 | 10 | 494 | 20 | 10 | 494 | 14 | Retry |
| 11 | 528 | 11 | 528 | 34 | 11 | 528 | 0 | No Retry |
| 12 | 576 | 12 | 578 | 50 | 12 | 578 | 2 | Retry |
| 13 | 624 | 13 | 624 | 46 | 13 | 624 | 0 | No Retry |
| 14 | 672 | 14 | 764 | 140 | 14 | 784 | 92 | Retry |
| 15 | 720 | 15 | 765 | 1 | 15 | 765 | 45 | Retry |
| 16 | 768 | 16 | 768 | 3 | 16 | 768 | 0 | No Retry |
| 17 | 816 | 17 | 818 | 48 | 17 | 816 | 0 | No Retry |
| 18 | 864 | 18 | 876 | 60 | 18 | 876 | 12 | Retry |
| 19 | 912 | 19 | 912 | 36 | 19 | 912 | 0 | No Retry |
| 20 | 960 | 20 | 960 | 48 | 20 | 960 | 0 | No Retry |

When reviewing the above table, the two left most columns, or columns 1 and 2 represent information associated with the signal transmitted by an ICD. The "packet to be sent" column in an example embodiment represents the transmitted data packets 402 of the exemplary embodiment of FIG. 4, whereas the "sent timing" column represents a time in milli-seconds (ms) each transmitted data packet 402 is sent by the ICD. Each "packet to be sent" is at a constant 48 ms interval. For example, at 0 ms, the packet is 0; at 48 ms, the packet is 1; at 96 ms, the packet is 2; at 480 ms, the packet is 10; and the like. While in this example 48 ms intervals are provided, in other examples the intervals are in a range of times including and between 1 milliseconds and 5 seconds. The "packet to be sent" in one example is also the unique identifier transmitted as part of the data packet.

Columns 3, 4 and 5 of Table 1 represent information associated with each signal received by the EI 504. In one example embodiment, the signal received is the received data packet 406 described in relation to FIG. 4. Column 3, the "packet received" column represents in real time the received packet number that is received as identified by the unique identifier. Column 4, the "receiving time (in ms)"

of each packet. Thus, in Column 3, when packets are received out of transmitted order, such as when the data packet with the unique identifier 6 was received before the data packet with unique identifier 5, the algorithm of the processor reorders the received data packets into the order in which they were actually intended to be transmitted. Column 7, the "received timing reordered" column, similar to Column 6 provides the time from start the data packet with a given unique identifier is received. Column 8, the "delta from expected timing" column represents the difference between the time from start the data packet is received compared to when the data packet is expected to be received based on the constant transmission interval. For example, the "delta from expected timing" for data packet 4 is determined by taking the actual time the data packet was received from the start, 192 ms compared to the expected receipt time in reference to Column 2, 192 ms. Thus, the "delta from expected timing" for data packet 4 is 0. For data packet 5, the packet was delayed and was received 330 ms from the start, while the expected time of receipt (as indicated by Column 2) was 240 ms, therefore the "delta from expected timing" for data packet 5 is 90 ms. Meanwhile, for reordered data packet 6, the actual time the data packet was received was at 320 ms while the expected time of receipt from the start was 288 ms, providing a 32 ms "delta from expected timing" for data packet 6. By reordering and utilizing the unique identifiers, the timing of the receipt of each data packet is determined without miscalculation as a result of delayed data packets.

Column 9 of Table 1 is a "comment" column that indicate whether a delay in receiving any given data packet occurs. Thus, when a "delta from expected timing" is not a zero value, the "comment" column indicates a retry data packet has been transmitted. In one example embodiment, the retry data packet is the retransmitted data packet 404 of FIG. 4.

Therefore, in one example, as described above, the delta time is calculated as the difference between the actual time Tn a packet is received verses the expected time (Toffset−48n for the table above), where Toffset is the time of the first arrived packet. Similarly, in the example, if the delta time is a negative number, the negative value is used for a new offset. Consequently, self-correction is provided. Additionally, periodically, that in one example is once a minute, the algorithm of the EI 504 does a self-calibration to address potential timing drift. Specifically, the algorithm of the EI 504 takes one arrival time and sets it as Toffset, and then continues data collection.

Alternatively, the IMD and EI can re-negotiate timing to re-synch periodically, or when needed.

Based on the amount of detected retry data packets, and the "delta form expected timing" determinations, histograms may be formed to inform a user of the quality of the communication link. In general, the quality of the communication is a function of the expected time, the received time, and can be expressed for example Q (arrival time variance based)=f (expected event times, received event times, the event orders).

In one such example, the EI 504 establishes a first-in-first-out (FIFO) histogram that in one example has 7 bins, with the center at 0 ms, as the received time when there is no interference. One example of the 7 bin histogram is shown in the table below:

TABLE 2

| Bin   | 1    | 2        | 3        | 4        | 5        | 6        | 7   |
|-------|------|----------|----------|----------|----------|----------|-----|
| Range | <=10 | 10 to <=20 | 20 to <=30 | 30 to <=40 | 40 to <=50 | 50 to <=70 | 70< |

Thus, bin 1 represents every "delta from expected timing", or delta time that is equal to or less than 10 ms. Bin 2 represents every delta time between 10 ms and 20 ms and so on. Therefore, all of the delta times are grouped together over time and based on the percentage of delta times residing in individual bins, a processor can include an algorithm to determine the quality of the communication link. As an example, if 100% of the delta times are in bin 1, then the quality of the communication link is ideal. If only 90% of delta times are in bin 1 and 5% are within bins 5-7, the communication link is considered significantly worse than the ideal quality communication link, or to have reduced quality.

Similarly, in an alternative example as illustrated below in Table 3 a similar FIFO histogram is constructed by the EI 504 also with 7 bins, only in the example the center at 48 ms as the received time when there is no interference. Therefore, any time difference that is smaller than 48 ms is considered as no interference even though it may still have interference. As illustrated in the table below:

TABLE 3

| Bin   | 1    | 2       | 3       | 4       | 5       | 6        | 7    |
|-------|------|---------|---------|---------|---------|----------|------|
| Range | <=58 | 58 <= 68 | 68 <= 78 | 78 <= 88 | 88 <= 98 | 98 <= 108 | 108< |

Thus, in the example a reordered Column 5 "delta arrival timing" data, or delta arrival time, is utilized in creating the bins. When reviewing delta arrival time, bin 1 includes delta arrival times less than or equal to 58 ms, bin 2 is for delta arrival times between 58 ms and 68 ms, bin 3 is for delta arrival times between 68 ms and 78, and the like. Still, again similar to the previous example, the percentage of received signals in each bin is utilized to determine the quality of the communication link.

Additionally, a rolling standard deviation score can be calculated to reflect how well the data is or is not affected with timing. Specifically, the determination is made regarding how large of an effect is on the data transmission.

For each example formation of the histogram, the EI 504 forms the FIFO histogram with 7 bins, based on data packets received over a 5 second period. In another embodiment the FIFO histogram is formed based on data packets received in a range between 1-10 seconds in order to control the smoothness and quickness of the communication quality indicator. In an example, 5 seconds corresponds to about 104 events. Thus, when the desired number of events is reached, the histogram starts the FIFO process. Then, when a new event occurs, an increase of 1 is provided in the corresponding bin of the histogram, while a decrease of 1 is provided for the corresponding bin of the histogram for the earliest event recorded. The process is then repeated for each event. When there is no event arrived at the expected time, the corresponding bins are also decremented.

Thus, a communication quality indicator is able to be determined using a communication quality (Q) variation that is based on the variation in time of the received data packet. In an example utilizing a FIFO containing 104 events, as illustrated in the above histogram of Table 3 the Q variation can be set to 5 if 93 or more of the 104 events (at least 90%) indicate the data packet is received in 58 ms or less. If the condition is not met, a determination is then made regarding whether 100 or more (at least 96%) of the received data packets are in bins 1 and 2, or were received in 68 ms or less. Again, in other words, if 96% of the received signals are received in a time interval of 68 ms or less, the condition is met. If the condition is not met, then the next determination is made whether bin 1+bin 2+bin 3>/=103 (or 99%) of the total events. If also accurate, all of the conditions are met, and the Q variation is set to 5. Thus, in the example, the IEGM would be streaming with 99% of packets received without recognizable delays, therefore indicating a very good IMD 502 with the capability for additional data transmission and resisting interference. Thus, in the example, all 5 lights 514, 516, 518, 520, and 522 of the light indicator 508 would light.

Similarly, Q variation is 4 if bin 1+bin 2>/=93 (or 90%) of the total events; bin 1+bin 2+bin 3>/=100 (or 96%) of the total events; and bin 1+bin 2+bin 3+bin 4>/=103 (or 99%) of the total events. Again, with streaming at 99% of packets in 88 ms or less, the capability of the IMD for additional data transmission and resisting interference is provided. Additionally, when Q variation is 4, 4 lights 514, 516, 518, and 520 of light indicator would light.

Q variation is 3 when bin 1+bin 2+bin 3>/=93 (or 90%) of the total events; bin 1+bin 2+bin 3+bin 4>/=100 (or 96%) of the total events; and bin 1+bin 2+bin 3+bin 4+bin 5>/=103 (or 99%) of the total events. Here, 96% of packets are streamed with 88 ms, indicating some capability of the IMD 502 for additional data transmission and resisting interference. Additionally, when Q variation is 3, 3 lights 514, 516, and 518 of light indicator would light.

Q variation is 2 when bin 1+bin 2+bin 3+bin 4>/=93 (or 90%) of the total events; bin 1+bin 2+bin 3+bin 4+bin 5>/=100 (or 96%) of the total events; and bin 1+bin 2+bin 3+bin 4+bin 5+bin 6>/=103 (or 99%) of the total events. Here, only 90% of packets are streamed in 88 ms, indicating that the IMD 502 has limited capability for additional data transmission and resisting interference. Additionally, when Q variation is 2, 2 lights 514 and 516 light.

Q variation is 1 when bin 1+bin 2+bin 3+bin 4+bin 5>/=93 (or 90%) of the total events; bin 1+bin 2+bin 3+bin 4+bin 5+bin 6>/=100 (or 96%) of the total events; and bin 1+bin 2+bin 3+bin 4+bin 5+bin 6+bin 7>/=103 (or 99%) of the total events. Here, only 80% of packets are streamed in 88 ms, indicating the IMD 502 has the capability of having a broken real time EGM transmission. Additionally, when Q variation is 1, only 1 light 514 lights.

Q variation is 0 for all other combinations of bin 1+bin 2+bin 3+bin 4+bin 5+bin 6+bin 7. In such a case the streaming of the IMD 502 is likely to be intermittent and/or jittery.

In one example, the Q variation can be further modified by the rolling standard deviation score. For example, in the Q=5 case, in the last sub case for 3 bins, when bin 1+bin 2+bin 3>/=103 (or 99%) of the total events, the standard deviation score is calculated for these events. If the deviation is small, such as I<=25, for example, the Q is 5, otherwise the Q is downgraded to 4 from 5.

While in the examples 7 bins are utilized, in other example embodiments less than 7 bins are utilized. In yet other example embodiments, more than 7 bins are utilized. In yet, other example, the data in table delta from the expected timing is used for the histogram.

In another example embodiment relative received signal strength indicator (RSSI) is utilized to refine the communication quality indicator. Specifically, a unitless RSSI is the measure of the power present in a received radio signal. Specifically, in an example embodiment an RSSI number is provided in association with a predetermined decibel amount. Thus, the system collects the RSSI from the IMD 502 and from external sources and the communication quality Q RSSI is determined. In one example Q RSSI=5 if RSSI>x1 dBm (e.g. −40 dBm); Q RSSI=4 if RSSI>x2 dBm (e.g. −50 dBm); Q RSSI=3 if RSSI>x2 dBm (e.g. −60 dBm); Q RSSI=2 if RSSI>x2 dBm (e.g. −70 dBm); 0 RSSI=1 if RSSI>x2 dBm (e.g. −80 dBm); and Q RSSI=0 if RSSI>x2 dBm (e.g. −90 dBm). Thus, an alternative method of rating the streaming is presented. In addition, the two methods in one example are combined such that Q communication indicator=smaller of the Q Variation and the Q RSSI. Alternatively, the Q RSSI is a weighed average of the RSSI IMD and RSSI EI. Specifically, the Q (Variance) and Q RSSI can go through a weighed average to obtain the final Q score.

Figure 6:
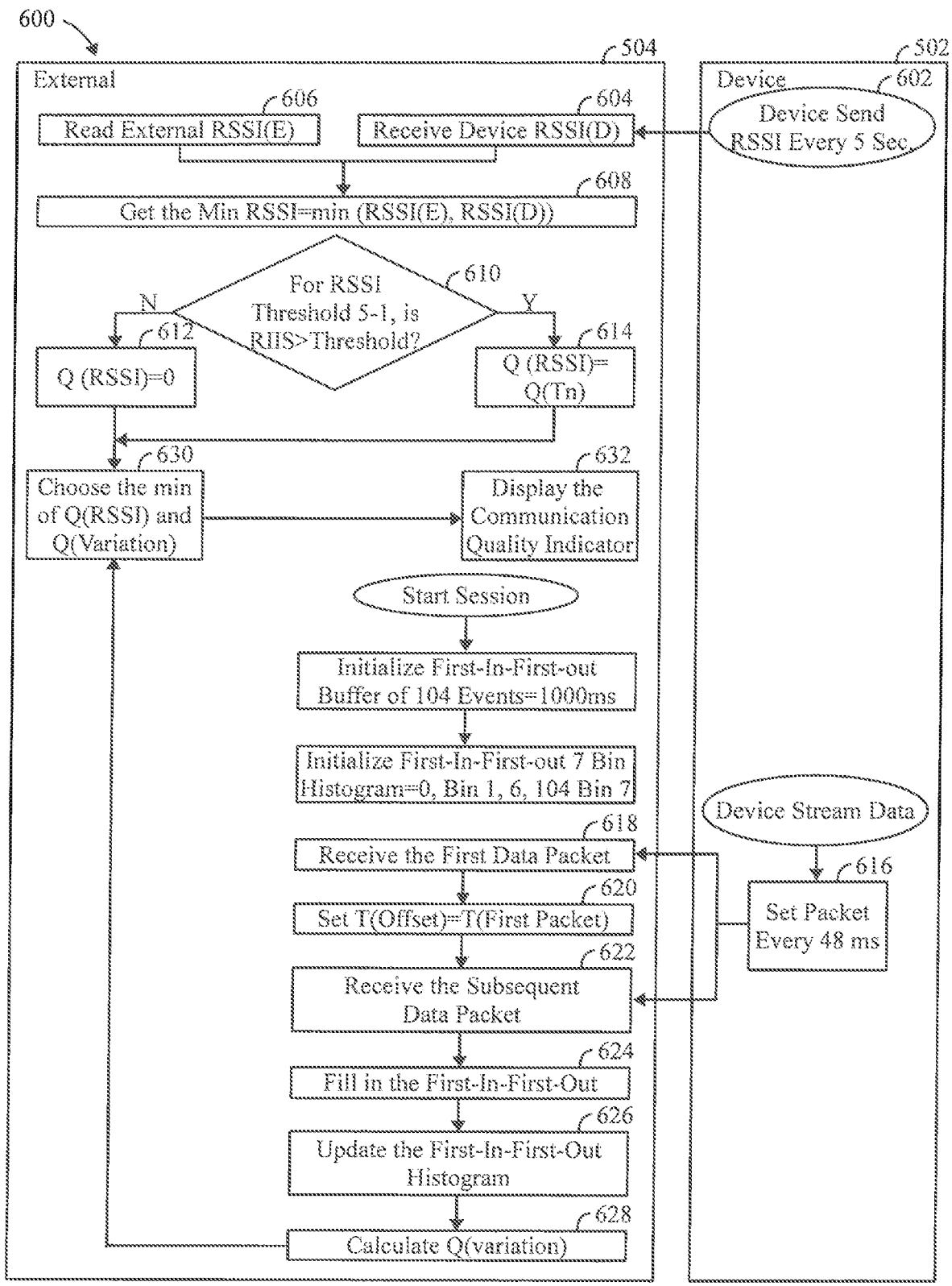
FIG. 6 illustrates a block flow chart of a method of determining quality of a communications link between an external instrument and an implantable medical device in accordance with embodiments herein.
Figure 7:
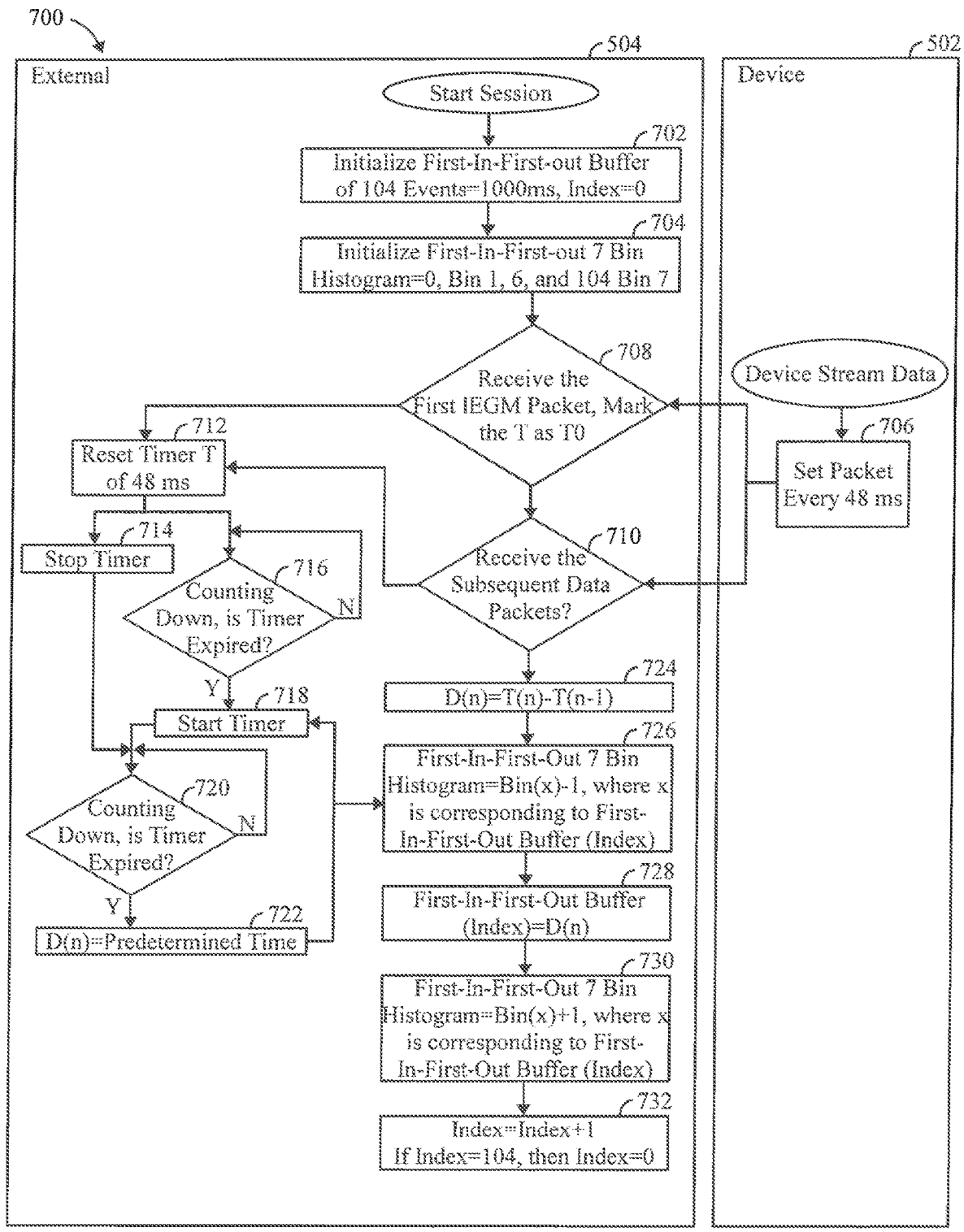
FIG. 7 illustrates a block flow chart of a method of forming a histogram in accordance with embodiments herein.

FIGS. 6 and 7 illustrate flowcharts of a method for forming a communication quality indicator utilized for evaluating the bi-directional communication link between the EI 201, 504 and the IMD 101, 502. The method may be implemented as a software algorithm, package, or system that directs one or more hardware circuits or circuitry to perform the actions described herein. For example, the operations of the method may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic.

FIG. 6 illustrates a flowchart for a method 600 performed by the EI 201, 504 to form a communication quality indicator based on timing of signals received the EI 201, 504 from the IMD 101, 502. In the method 600 two separate methods are utilized to determine a communication quality indicator. The two different determinations are then compared, and the minimum value is chosen to be displayed. Alternatively, a weighted average is used to determine the final score of the quality indicator for the display. At 602, the processor of the IMD 101, 502 periodically sends a packet of data from which the power of the signal, or RSSI can be determined. In one example, the packet of data is sent by the IMD 101, 502 every five (5) seconds. In another embodiment, the packet of data is sent by the IMD 101, 502 every four (4) seconds. The processor of the EI 201 in one example is the CPU 352 of the communication subsystem 330 the utilizes communication circuit 354 of FIG. 3. At 604, the processor of the EI 201, 504 receives the packet of data and determines a device RSSI. At 606, the processor of the EI 201, 504 receives external signals and determines an external RSSI. At 608, the processor of the EI gets the min value when comparing the external RSSI and the device RSSI. In one example a comparator compares the external RSSI and device RSSI.

At. 610, the processor of the EI 201, 504 makes a decision regarding whether for an RSSI threshold of 5-1, whether the selected RSSI is greater than a predetermined threshold. If no, at 612, the communication quality indicator Q(RSSI)=0. If at 610, a threshold level is met, at 614, the communication quality indicator Q(RSSI)=Q(Tn). In other words, if the minimum RSSI obtained at 608 has an RSSI above the 3 threshold, but below the 4 threshold:then at decision 610 the answer is yes and at 614 Q(Tn)=Q(3)=0. However, if at 610 a threshold level is not above 1, then no threshold level is met, and at 610 the decision is no. Thus, at 612, the communication quality indicator is set at Q(RSSI)=0.

While the processor of the EI 201, 504 makes the determinations, at 616 the processor of the IMD 101, 502 also periodically streams additional packets of data. In one example the packets of data are IEGMs streamed every 48 ms. At 618, the processor of the EI 201, 504 receives a first data packet. In one example the data packet is an IEGM data packet. At 620, the processor of the EI 201, 504, sets the time offset to be equal to the time to receive the first data packet, or Set T(offset)=T (first packet). At 622, the processor of the EI 201, 504 receives an additional or subsequent data packet and determines a delta time. Again, in one example the additional data packet is an IEGM data packet. At 624, the processor of the EI 201, 504 provides the delta time to a memory of the EI 201, 504. In an example embodiment, the memory is a first in first out (FIFO) buffer. At 626, the processor of the EI 201, 504 updates a histogram within the memory. In one example, the histogram is a first in first out (FIFO) histogram. At 628, the processor of the EI 201, 504 responsive to the updated histogram calculates a communication quality indicator based on time variation, or Q(variation). At 630, the processor of the EI compares the communication quality indicator determined by using the RSSI methodology, Q (RSSI), to the communication quality indicator determined by using the time variation methodology Q(variation). From the comparison, the minimum value is selected. In one example a comparator compares the values and selects the minimum value, discarding the unused value. At 632, the processor of the EI 201, 504 displays the selected communication quality indicator on a user interface.

FIG. 7 illustrates a process 700 for generating a histogram in order to determine a communication quality indicator by using variations in time for receiving data packets from an IMD 101, 502 in accordance with an embodiment. At 702, a processor of the EI 201, 504 initializes a FIFO buffer of predetermined events during a predetermined amount of time, measured in the example in mili-seconds (ms), where index equals zero (0). In one example the FIFO buffer is 104 events=1000 ms, index=0. The processor of the EI 201 in one example is the CPU 352 of the communication subsystem 330 that utilizes communication circuit 354 of FIG. 3. At 704, the processor of the EI 201, 504 initializes a FIFO seven (7) bin histogram. At 706, the processor of the IMD 101, 502 periodically transmits data packets to the processor of the EI 201, 504. In one example embodiment a packet is sent every 48 ms. In another example embodiment the data packet is a streamed IEGM. At 708, the processor of the EI 201, 504 receives the data packet from the IMD 101, 502 and marks the time T as T0. At 710, the processor of the EI 201, 504 receives subsequent data packets from the processor of the IMD 101, 502.

At 712, the processor of the EI 201, 504 resets a timer T based on the measured time between data packets received at 708 and 710. In one example the time between the data packets received is 48 ms. At 714, flow from the resetting of the timer at 712 goes to stop the timer. At 716, flow from the resetting of the timer at 712 goes to determine if the timer has expired. At 718, if the timer has not expired, the processor of the EI 201, 504 again determines if the timer has expired. If at 716, yes, the timer has expired, then at 718 the processor of the EI starts the timer over. At 720, a decision is made by the processor of the EI to determine if the timer has expired. If no, the timer is stopped at 712. If at 720, yes, and the timer has expired, then at 722 the processor of the EI 201, 504 sets D(n)=a predetermined time that in one example is 1000 ms. After the processor of the EI 201, 504 sets D(n)=a predetermined time, the processor at 718 starts the timer.

At 724, after subsequent data packets at 710 are received by the processor of the EI 201, 504, the processor of the EI 201, 504 sets D(n)=T(n)−T(n−1). At 726, the FIFO 7 bin histogram=Bin(x)−1, where x corresponds to the FIFO buffer, or an index. At 728, the processor of the EI 201, 504 sets the FIFO buffer (index)=D(n). At 730, the processor of the EI 201, 504 sets the FIFO 7 bin histogram=Bin(x)+1, where x corresponds to the FIFO buffer (index). At 732, the processor of the EI 201, 504 sets the index=index+1 and if index=a predetermined count, then the index=0. In one example embodiment the predetermined count is 104. Therefore, a difference between expected time intervals and actual time intervals of previous data packets and subsequent data packets is continually calculated to continually update the histogram, providing up to date information to a user. Thus, a histogram is formed. The histogram information is further calculated to obtain the quality score Q. The final Q=f (Q (variance), Q (RSSI IMD), Q (RSSI EI). The Quality score is then presented that may be used by a physician in determining potential interference during a procedure. By utilizing a variable of the received signal, and specifically variance in time of the signal received, a direct measurement of signal interference is taken. Consequently, greater accuracy of signal strength and corresponding interference is achieved.

CLOSING

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for determining quality of a communications link between an external instrument (EI) and an implantable medical device (IMD), the method comprising:
   receiving, with a receiver of an EI, a data packet stream sent at intervals from an IMD;
   determining, with a processor of the EI, an expected time interval between a first data packet and a second data packet within the data packet stream;
   determining, with the processor of the EI, a difference between the expected time interval between the first data packet and the second data packet and an actual time interval between the first data packet and the second data packet; and
   providing, with the processor of the EI, a time variant communication quality indicator based on the difference between the expected time interval between the first data packet and the second data packet and the actual time interval between the first data packet and the second data packets,
   wherein one of the first and second data packets represents a retransmitted data packet, wherein the actual time interval includes a delay due to retransmission, the retransmission creating the difference between the expected and actual time intervals.

2. The method of claim 1, further comprising: determining, with the processor of the EI, a relative received signal strength indicator (RSSI) of each data packet received by the receiver of the EI;
   calculating, with the processor of the EI, a RSSI communication quality indicator based on the RSSI of each data packet received by the receiver of the EI;

comparing, with the processor of the EI, the time variant communication quality indicator and the RSSI communication quality indicator;

selecting, with the processor of the EI, one of the time variant communication quality indicator, the RSSI communication quality indicator, or a weighted combination of the time variant communication quality indicator or the RSSI communication quality indicator to present to a user.

3. The method of claim 1, wherein the time variant communication quality indicator is presented through a light indicator.

4. The method of claim 1, wherein a communication subsystem of the EI presents the time variant communication quality indicator through a user interface.

5. The method of claim 1, wherein the first and second data packets are streamed intracardiac electrograms (IEMGs), the time variant communication quality indicator indicative of a time variance between received IEGM data packets.

6. The method of claim 1, wherein the intervals are in a range of times including and between 1 milliseconds and 5 seconds.

7. The method of claim 1, further comprising:
after determining the difference between the expected time interval between the first data packet and the second data packet and the actual time interval between the first data packet and the second data packet, determining a difference between expected time intervals and actual time intervals between subsequent data packets and previous data packets; and
forming a histogram based on determining the difference between the expected time intervals and actual time intervals between subsequent data packets and previous data packets.

8. The method of claim 7, wherein the histogram is formed using a first-in-first-out buffer.

9. The method of claim 1, further comprising establishing a communications link between the EI and IMD; the receiver of the EI receiving the data packet stream with the first and second data packets over the communications link during a communications session.

10. A method for determining quality of a communications link between an external instrument (EI) and an implantable medical device (IMD), the method comprising:
receiving, with a receiver of an EI, data packets sent at intervals from an IMD; determining, with a processor of the EI, the difference in time between a subsequent data packet and a previous data packet;
providing, with the processor of the EI, a time variant communication quality indicator based the difference in time between the subsequent data packet and the previous subsequent data packet;
determining, with the processor of the EI, a relative received signal strength indicator (RSSI) of the subsequent data packet received by the receiver of the EI;
calculating, with the processor of the EI, a RSSI communication quality indicator based on the RSSI of the subsequent data packet received by the receiver of the EI;
comparing, with the processor of the EI, the time variant communication quality indicator and the RSSI communication quality indicator; and
selecting, with the processor of the EI, one of the time variant communication quality indicator and the RSSI communication quality indicator to present to a user.

11. The method of claim 10, wherein the lower of the time variant communication quality indicator and the RSSI communication quality indicator weighted combination of the time variant communication quality indicator or the RSSI communication quality indicator is selected.

12. The method of claim 10, wherein the selected communication quality indicator is presented through a light indicator having up to five lights.

13. The method of claim 10, wherein the data packets are streamed intracardiac electrograms (IEMGs).

14. The method of claim 10, wherein the constant interval is in a range of times including and between 1 milliseconds and 5 seconds.

15. The method of claim 10 wherein the EI utilizes a Bluetooth low energy protocol.

16. An external instrument (EI) that monitors an implantable medical device (IMD), comprising:
a receiver for receiving a data packet stream sent by the IMD; and
a processor configured to determine a communication quality indicator based on delays between successive data packets of the data packet stream, received by the EI, wherein one of the successive data packets represents a data packet that is retransmitted, wherein the delays include a first delay due to the retransmission, wherein the retransmission creates a difference between expected and actual time intervals.

17. The EI of claim 16, wherein the IMD is a cardioverter-defibrillator.

18. The EI of claim 16, wherein the EI utilizes a Bluetooth low energy protocol.

19. The EI of claim 16, wherein the processor is further configured to determine a communication quality indicator based on relative received signal strength indicator (RSSI) of each data packet received by the EI.

20. The EI of claim 19, further comprising: a comparator that compares the communication quality indicator based on delays between packets received by the EI to the communication quality indicator based on relative received signal strength indicator (RSSI) of each data packet received by the EI and selects the communication quality indicator with a minimum value.

21. The EI of claim 16, wherein the data packets are periodically sent at an interval.

22. The method of claim 16, further comprising:
prior to the establishing the communications session, entering a scanning state; and
during the scanning state, receiving an advertisement packet at one of the EI or IMD, the advertisement packet transmitted from the other one of the EI or IMD; and
initiating the communications session based on the advertisement packet.

23. The EI of claim 16, wherein the processor is further configured to establish a communications link between the EI and IMD, and the receiver of the EI is configured to receive the data packet stream with the successive data packets over the communications link during a communications session.

24. The EI of claim 23, wherein the processor is further configured to:
enter a scanning state prior to establishing the communications session;
during the scanning state, receive an advertisement packet, the advertisement packet transmitted from the IMD; and initiate the communications session based on the advertisement packet.

\* \* \* \* \*